United States Patent
Butts et al.

(10) Patent No.: US 6,506,371 B1
(45) Date of Patent: *Jan. 14, 2003

(54) SILICONE COMPOSITIONS FOR PERSONAL CARE PRODUCTS AND METHOD FOR MAKING

(75) Inventors: Matthew David Butts, Rexford, NY (US); Susan Adams Nye, Feura Bush, NY (US); Christopher Michael Byrne, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/616,533

(22) Filed: Jul. 14, 2000

(51) Int. Cl.$^7$ .................................................. A61K 7/06
(52) U.S. Cl. .................................... 424/70.1; 424/70.12
(58) Field of Search .............................. 424/70.1, 70.12

(56) References Cited

U.S. PATENT DOCUMENTS

| | | |
|---|---|---|
| 4,567,039 A | 1/1986 | Stadnick et al. |
| 4,859,460 A | 8/1989 | Mahieu et al. |
| 4,973,475 A | 11/1990 | Schnetzinger et al. |
| 5,030,756 A | 7/1991 | Deppert et al. |
| 5,087,733 A | 2/1992 | Deppert et al. |
| 5,160,733 A | 11/1992 | Berthiaume |
| 5,206,013 A | 4/1993 | Deppert et al. |
| 5,211,942 A | 5/1993 | Deppert et al. |
| 5,248,783 A | 9/1993 | O'Lenick |
| 5,254,335 A | 10/1993 | Deppert et al. |
| 5,280,099 A | 1/1994 | Imperante et al. |
| 5,350,572 A | 9/1994 | Savaides et al. |
| 5,523,080 A | 6/1996 | Gough et al. |
| 5,525,332 A | 6/1996 | Gough et al. |
| 5,609,856 A | 3/1997 | Dubief et al. |
| 5,609,861 A | 3/1997 | Dubief et al. |
| 5,969,077 A | 10/1999 | Schrock et al. |

FOREIGN PATENT DOCUMENTS

| | | |
|---|---|---|
| EP | 0159628 | 4/1985 |
| EP | 0275707 A2 | 7/1988 |
| EP | 0509922 | 4/1992 |
| EP | 0784068 A1 | 7/1997 |
| WO | 9935180 | 12/1997 |
| WO | 9838974 | 4/1998 |
| WO | 0040210 | 1/2000 |
| WO | WO 00/40210 * | 7/2000 |

OTHER PUBLICATIONS

"Development of Novel Attachable Initiator for "Living" radical Polymerization and Synthesis of Polysiloxane Block Copolymer", Nakagawa and Matyjaszewski, Amer. Chem. Soc., Polym. Preprints 1996, 270–271.

* cited by examiner

*Primary Examiner*—Thurman K. Page
*Assistant Examiner*—Blessing Fubara
(74) *Attorney, Agent, or Firm*—Bernadette M. Bennett; Noreen C. Johnson

(57) ABSTRACT

A composition and method for making a silicone composition is provided which comprises at least one polysiloxane or silicone resin, at least one molecular hook, and at least one linker.

45 Claims, No Drawings

SILICONE COMPOSITIONS FOR PERSONAL CARE PRODUCTS AND METHOD FOR MAKING

BACKGROUND OF THE INVENTION

The present invention relates to compositions for personal care products. More particularly, the present invention relates to silicone compositions which achieve conditioning benefits in hair care products.

Silicones are widely used in hair care products due to the conditioning benefit that they impart to hair. By modern day technology, the silicone is deposited on hair during the application process but is held only by weak physical forces, such as hydrogen bonding or van der Waals interactions. Generally, conditioning benefits are attributed to the deposition of high molecular weight, high viscosity fluids and gums which can weigh down the hair. Because the interactive forces are weak, the benefits of silicone by deposition are short lived. Beneficial conditioning effects can also be caused by treating hair with silanol capped amino-functionalized silicones. These can undergo condensation cure reactions on hair to form somewhat durable films.

It is widely known by those skilled in the art that covalent bonding is one key to "permanent" hair treatment. Processes which alter the structure of the hair, such as permanent wave and color treatment methods, do provide longer lasting effects. These processes include glycolate reduction and peroxide reoxidation. A significant disadvantage of these processes is that they are very damaging to hair and can only be carried out infrequently.

Gough et al. in U.S. Pat. Nos. 5,523,080 and 5,525,332 describe the synthesis of silicone-azlactone polymers which exhibit covalent bonding and "permanent" conditioning benefit. Gough et al. discuss incorporating an azlactone-functionalized copolymer which consists of vinylazlactone and methacryloyl polydimethylsiloxane monomers into a silicone-active group-hair structure. The hair treatment using the silicone-azlactone polymers did not consist of the steps of reduction with a glycolate or reoxidation with peroxide.

It is desirable to produce silicone compositions which can be used to treat damaged hair and provide durable benefits. Thus, silicone products are constantly being sought which can both covalently bond to hair as well as impart hair care benefits appreciated by consumers.

BRIEF SUMMARY OF THE INVENTION

The present invention provides a composition and method for making a silicone composition which comprises at least one polysiloxane or silicone resin, at least one molecular hook, and at least one linker wherein the linker comprises at least one moiety of the formulas (I), (II), (III), (IV), (V), or (VI):

(I)

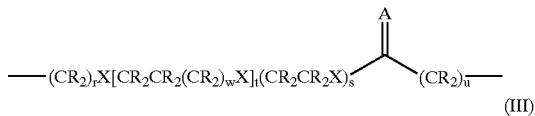
(II)

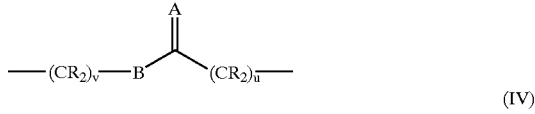
(III)

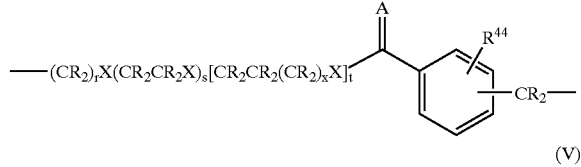
(IV)

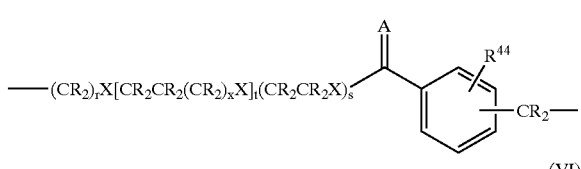
(V)

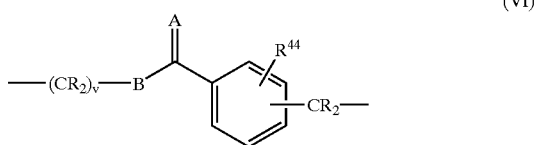
(VI)

wherein r is in a range between about 1 and about 10;
wherein s is in a range between about 0 and about 100;
wherein t is in a range between about 0 and about 100;
wherein u is in a range between about 1 and about 10;
wherein v is in a range between about 1 and about 10;
wherein w is 1 or 2;
wherein x is 1 or 2;
wherein X is O, NOH, NOR. or NR;
wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;
wherein $R^{44}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;
A=O, NOH, NOR, NR or S:
B=O, NOH, NOR, NR or S:
and where the polysiloxane or the silicone resin is bound to the $(CR_2)_r$ (Formula I, II, IV, and V) or $(CR_2)_v$ (Formula III and VI).

The present invention includes a silicone composition having the formula:

$$M_a M'_b D_c D'_d T_e T'_f Q_g$$

where the subscripts a, b, c, d, e, f and g are zero or a positive integer object to the limitation that the sum of the subscripts b, d and f is one or greater; where M has the formula:

$$R^{39}{}_3 SiO_{1/2},$$

M' has the formula:

$$(Z-Y)R^{40}{}_2SiO_{1/2},$$

D has the formula:

$$R^{41}{}_2SiO_{2/2},$$

D' has the formula:

$$(Z-Y)R^{42}SiO_{2/2},$$

T has the formula:

$$R^{43}SiO_{3/2},$$

T' has the formula:

$$(Z-Y)SiO_{3/2},$$

and Q has the formula $SiO_{4/2}$, where each $R^{39}$, $R^{40}$, $R^{41}$, $R^{42}$, $R^{43}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, or may contain amino groups to form aminoalkyls, for example aminopropyl or aminoethylaminopropyl, or may contain polyether units of the formula $(CH_2CHR^{45}O)_k$ where $R^{45}$ is $CH_3$ or H and k is in a range between about 4 and about 20; Z, independently at each occurrence, represents a molecular hook; and Y, independently at each occurrence, represents a linker. The term "alkyl" as used in various embodiments of the present invention is intended to designate both normal alkyl, branched alkyl, aralkyl, and cycloalkyl radicals. Normal and branched alkyl radicals are preferable those containing in a range between about 1 and about 12 carbon atoms, and include as illustrative non-limiting examples methyl, ethyl, propyl, isopropyl, butyl, tertiary-butyl, pentyl, neopentyl, and hexyl. Cycloalkyl radicals represented are preferably those containing in a range between about 4 and about 12 ring carbon atoms. Some illustrative non-limiting examples of these cycloalkyl radicals include cyclobutyl, cyclopentyl, cyclohexyl, methylcyclohexyl, and cycloheptyl. Preferred aralkyl radicals are those containing in a range between about 7 and about 14 carbon atoms; these include, but are not limited to, benzyl, phenylbutyl, phenylpropyl, and phenylethyl. Aryl radicals used in the various embodiments of the present invention are preferably those containing in a range between about 6 and about 14 ring carbon atoms. Some illustrative non-limiting examples of these aryl radicals include phenyl, biphenyl, and naphthyl. An illustrative non-limiting example of a halogenated moiety suitable is trifluoropropyl.

DETAILED DESCRIPTION OF THE INVENTION

The present invention comprises a silicone composition which includes at least one polysiloxane or silicone resin, at least one linker, and at least one molecular hook. The linker is bound to both a molecular hook and to an atom of a polysiloxane or silicone resin. Preferably the linker is bound to a polysiloxane or silicone resin through a silicon (Si), carbon (C), oxygen (O), nitrogen (N), or sulfur (S) atom, and most preferably through a silicon atom. When more than one linker is present, it is also contemplated that linkers may be bound to a polysiloxane or silicone resin through more than one type of atom, for example through both silicon and carbon atoms.

The present invention includes at least one polysiloxane or silicone resin having the formula:

$$M_aM'_bD_cD'_dT_eT'_fQ_g$$

where the subscripts a, b, c, d, e, f and g are zero or a positive integer, subject to the limitation that the sum of the subscripts b, d and f is one or greater; where M has the formula:

$$R^{39}{}_3SiO_{1/2},$$

M' has the formula:

$$(Z-Y)R^{40}{}_2SiO_{1/2},$$

D has the formula:

$$R^{41}{}_2SiO_{2/2},$$

D' has the formula:

$$(Z-Y)R^{42}SiO_{2/2},$$

T has the formula:

$$R^{43}SiO_{3/2},$$

T' has the formula:

$$(Z-Y)SiO_{3/2},$$

and Q has the formula $SiO_{4/2}$, where each $R^{39}$, $R^{40}$, $R^{41}$, $R^{42}$, $R^{43}$ is independently at each occurrence a hydrogen atom, $C_{1-22}$ alkyl, $C_{1-22}$ alkoxy, $C_{2-22}$ alkenyl, $C_{6-14}$ aryl, and $C_{6-22}$ alkyl-substituted aryl, and $C_{6-22}$ aralkyl which groups may be halogenated, for example, fluorinated to contain fluorocarbons such as $C_{1-22}$ fluoroalkyl, or may contain amino groups to form aminoalkyls, for example aminopropyl or aminoethylaminopropyl, or may contain polyether units of the formula $(CH_2CHR^{45}O)_k$ where $R^{45}$ is $CH_3$ or H and k is in a range between about 4 and about 20; Z, independently at each occurrence, represents a molecular hook; and Y, independently at each occurrence, represents a linker. The term "alkyl" as used in various embodiments of the present invention is intended to designate both normal alkyl, branched alkyl, aralkyl, and cycloalkyl radicals. Normal and branched alkyl radicals are preferably those containing in a range between about 1 and about 12 carbon atoms, and include as illustrative non-limiting examples methyl, ethyl, propyl, isopropyl, butyl, tertiary-butyl, pentyl, neopentyl, and hexyl. Cycloalkyl radicals represented are preferably those containing in a range between about 4 and about 12 ring carbon atoms. Some illustrative non-limiting examples of these cycloalkyl radicals include cyclobutyl, cyclopentyl, cyclohexyl, methylcyclohexyl, and cycloheptyl. Preferred aralkyl radicals are those containing in a range between about 7 and about 14 carbon atoms; these include, but are not limited to, benzyl, phenylbutyl, phenylpropyl, and phenylethyl. Aryl radicals used in the various embodiments of the present invention are preferably those containing in a range between about 6 and about 14 ring carbon atoms. Some illustrative non-limiting examples of these aryl radicals include phenyl, biphenyl, and naphthyl. An illustrative non-limiting example of a halogenated moiety suitable is trifluoropropyl.

The polysiloxanes or silicone resins of the present invention are typically prepared by the hydrosilylation of an organohydrogen silicone having the formula:

$$M_aM^H{}_bD_cD^H{}_dT_eT^H{}_fQ_g$$

where the subscripts a, b, c, d, e, f and g are zero or a positive integer, subject to the limitation that the sum of the subscripts b, d and f is one or greater; M, D, T and Q are defined as above;

$M^H$ has the formula:

$$R^{40}_{3-h}H_hSiO_{1/2},$$

$D^H$ has the formula:

$$H_{2-i}R^{42}_iSiO_{2/2},$$

$T^H$ has the formula:

$$HSiO_{3/2},$$

where each $R^{40}$ and $R^{42}$ is independently as defined above; subscript h is in a range between 1 and 3; and subscript i is 0 or 1.

Hydrosilylation is typically accomplished in the presence of a suitable hydrosilylation catalyst. The catalysts preferred for use with these compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). A preferred catalyst contains platinum. Persons skilled in the art can easily determine an effective amount of platinum catalyst. Generally, an effective amount is in a range between about 0.1 parts per million and about 50 parts per million of the total silicone composition.

The organohydrogen silicone compounds that are the precursors to the compounds of the present invention may be prepared by the process disclosed in U.S. Pat. No. 5,420,221. The '221 patent discloses the redistribution of polydimethylsiloxane polymers with organohydrogen silicone polymers and optionally, added chain stopper, to provide a silicone with randomly-distributed hydride groups using a Lewis acid catalyst, preferably a phosphonitrilic compound.

Synthesis of the polysiloxane or silicone resin may also be performed by other method known to those skilled in the art, for example, the hydrosilylation of a monomer such as methyldichlorosilane could be followed by co-hydrolysis with the appropriate dialkyldichlorosilane and optionally, chlorotrimethylsilane It is to be noted that as pure compounds the subscripts describing the organohydrogen siloxane precursor and the hydrosilylation adduct of the present invention are integers as required by the rules of chemical stoichiometry. The subscripts will assume non-integral values for mixtures of compounds that are described by these formulas. The restrictions on the subscripts heretofore described for the stoichiometric subscripts of these compounds are for the pure compounds, not the mixtures.

In specific embodiments of the present invention, the silicone composition typically comprises at least one compound of the following formulas, (VII), (VIII), (IX), (X), (XI), (XII), or (XIII)

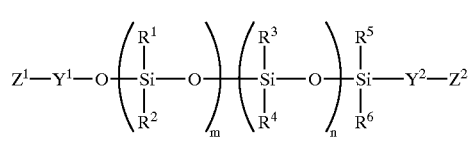
(VII)

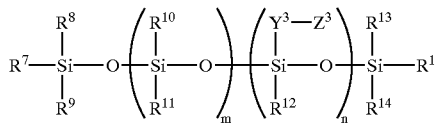
(VIII)

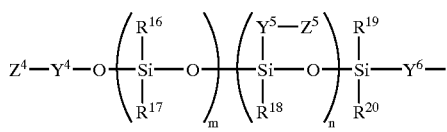
(IX)

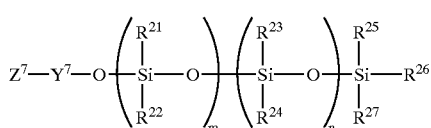
(X)

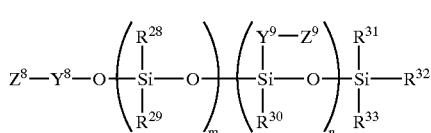
(XI)

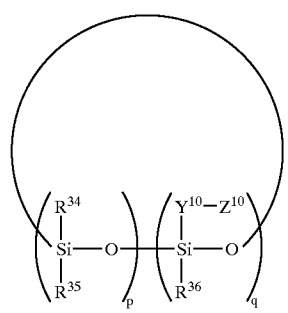
(XII)

$$(R^{37}_3SiO_{1/2})_a[(Z-Y)R^{38}_2SiO_{1/2}]_b(SiO_{4/2})_g \quad (XIII)$$

where each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, and $R^{38}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, may contain amino groups to form aminoalkyls, or may contain polyether units; $Z^1$–$Z^{11}$, independently at each occurrence, represents a molecular hook; and $Y^1$–$Y^{11}$, independently at each occurrence, represents a linker; wherein "m" in each formula has a value in a range between about 0 and about 13,000, preferably about 0 and about 1000, more preferably between about 1 and about 250, still more preferably between about 5 and about 250, even more preferably between about 10 and about 150, and most preferably between about 20 and about 120; "n" in each formula has a value in a range between about 0 and about 13,000, more preferably between about 0 and about 50, more preferably between about 1 and about 20, still more preferably between about 2 and about 10 with the proviso that in formula (VIII) "n" is not 0; "m+n" in each formula has a value in a range between about 1 and about 26,000, preferably in a range between about 3 and about 250, more preferably between about 5 to about 150, and most preferably between about 15 and about 120; "q" has a value of at least one; "p+q" has a value of at least 3, preferably in a range between about 3 and about 20, more preferably in a range between about 3 and about 10, and most preferably in a range between about 3 and 6; "a" has a value greater than or equal to one; and "b" and "g" have a value of at least one. $R^{1-38}$ is preferably methyl. The preferred silicone composition includes a compound of the formula (VII) or (VIII). The polysiloxane or silicone resin typically has a molecular weight in a range between about 100 and about 6,000,000, preferably in a range between about 250 and about 50,000, more preferably in a range between about 500 and about 25,000, and most preferably in a range between about 500 and about 15,000.

The number of Y—Z moieties on a polysiloxane or silicone resin in the composition is at least one. In preferred embodiments the average number of Y—Z moieties on a polysiloxane or silicone resin is in a range between about 1 and about 100, more preferably in a range between about 1 and about 20, still more preferably in a range between about 1 and about 10.

In one embodiment of the present invention, a polysiloxane- or silicone resin-containing composition includes a preponderance of a specific linear, branched, cross-linked, or cyclic polysiloxane or silicone resin. In other embodiments of the present invention, a polysiloxane- or silicone resin-containing composition comprises a mixture of polysiloxanes, mixture of silicone resins, or mixtures of polysiloxanes and silicone resins which may include linear, branched, cross-linked, and cyclic species. Also, suitable compositions may comprise one or more polysiloxanes and/or silicone resins which may contain adventitious amounts of other species, for example, arising during the synthesis process for said polysiloxanes or silicone resins, for example at a level in a range between about 0.0001 wt. % and about 5 wt. % based on total silicon-containing species. In illustrative examples, suitable compositions may contain adventitious amounts of $D_4$, or species containing Si—H, Si—OH, Si-O-alkyl bonds, and mixtures thereof.

The molecular hook may be selected from the range consisting of heterocyclic molecular hooks, $sp^2$ aliphatic trigonal carbon molecular hooks, $sp^3$ carbon molecular hooks, metal based molecular hooks, non-metal and metalloid based molecular hooks, energy-sensitive molecular hooks and mixtures thereof. The molecular hook is preferably selected from the range consisting of heterocyclic molecular hooks, $sp^2$ aliphatic trigonal carbon molecular hooks, $sp^3$ carbon molecular hooks and non-metal molecular hooks. The molecular hook is more preferably selected from heterocyclic molecular hooks, $sp^2$ aliphatic trigonal carbon molecular hooks and non-metal molecular hooks.

The molecular hook of the present invention preferably comprises a sulfur-containing compound wherein the sulfur-containing protective group may be a heterocyclic ring or ring system. Heterocyclic groups that are suitable for use in the present invention include mono- or polyunsaturated or saturated heterocyclic rings, heterocyclic ring systems, fused heterocyclic ring systems, substituted heterocyclic rings, substituted heterocyclic ring systems or substituted fused heterocyclic ring systems. The heterocyclic rings contain in a range between about three and about thirty members, and may contain electronegative heteroatoms including N, O, S, or P. The heterocyclic rings or ring systems also may contain exocyclic double bonds of the C=M type wherein M is O, S, $NE^1$ or $CE^1E^2$. $E^1$ and $E^2$ used here, and E, $E^3$, and $E^4$ used hereinafter, each represent, independently from one another, a monovalent group which can be a silicone group, H or any of the following: a straight, branched or mono- or polycyclic aliphatic, mono or polyunsaturated alkyl, aryl, heteroalkyl, heteroaliphatic or heteroolefinic system including carbon atoms in a range between about 1 and about 30 together with heteroatoms in a range between about 0 and about 15, especially O, N, S, P, Si, and can incorporate one or more substituents including, but not limited to, mono, poly or perfluoro substitution.

In particular, the molecular hook may be a heterocyclic pyridinium compound (XIII), a heterocyclic triazinium compound (XIV), a heterocyclic pyrimidinium compound (XV), or a heterocyclic pyrazine compound (XVI):

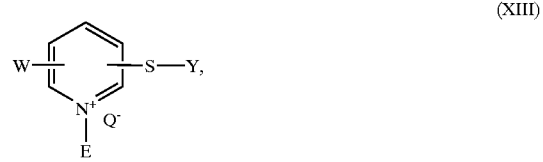

(XIII)

(XIV)

(XV)

(XVI)

wherein W represents optional substituents on the heterocyclic ring or ring system, Y represents the linker, $Q^-$ represents a counterion, and E is defined above. The preferred molecular hook is the pyrimidinium molecular hook of formula (XV).

Optional substituents, W, which can be present on the heterocyclic ring or ring system can be selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $N_2$, N=$NE^1$, N=$NOE^1$, $NE^1CN$, N=C=$NE^1$, $NE^1NE^2E^3$, $NE^1NE^2NE^3E^4$, $NE^1N$=$NE^2$; other miscellaneous groups including $CONE^1_2$, $CONE^1COE^2$, C(=$NE^1$)$NE^1E^2$, CHO, CHS, CN, NC, Hal, and derived groups that connect one or more of the optional substituents via a ring system; Hal is fluorine, chlorine, bromine, or iodine. E, $E^1$, $E^2$, $E^3$, and $E^4$ are defined above. The substituent E is preferably methyl.

The counterion, $Q^-$, can include halides, borates, phosphates, tosylates, mesylates, triflates, and other counterions known to those skilled in the art. $Q^-$ is preferably iodide, chloride, or bromide.

Typically, the linker precursor has the formulas (I) through (VI)

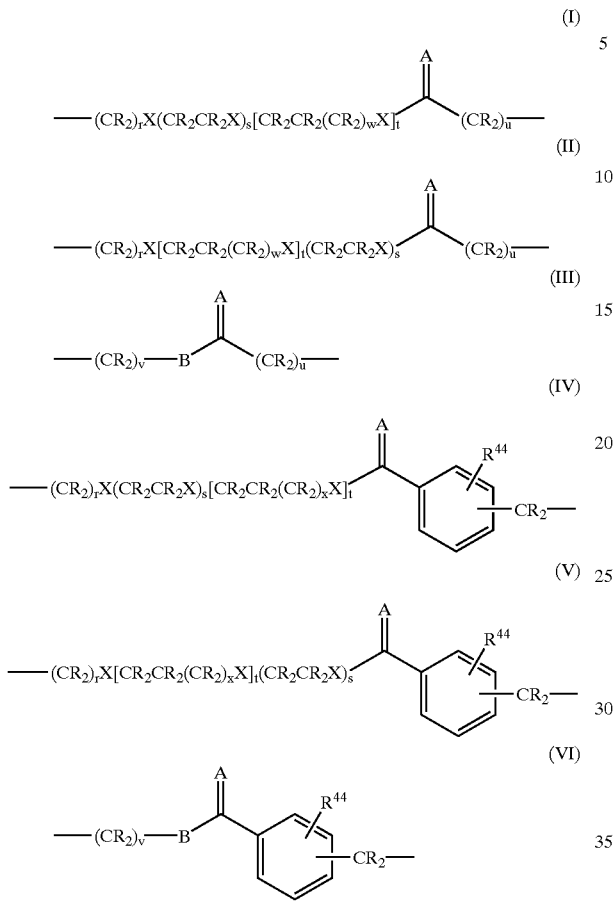

where r is in a range between about 1 and about 10, preferably 2 or 3;

s is in a range between about 0 and about 100, preferably 4 to 20;

t is in a range between about 0 and about 100, preferably in a range between about 0 and about 20, and most preferably 0;

u is in a range between about 1 and about 10, preferably 1;

v is in a range between about 1 and about 10, preferably 2 or 3;

w is 1 or 2;

x is 1 or 2;

X is O, NOH, NOR, or NR, preferably O;

wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;

wherein $R^{44}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen. $R^{44}$ is preferably H. If $R^{44}$ represents an aryl group, it can be fused to the ring in Formulas (IV) through (VI);

A=O, NOH, NOR, NR or S, preferably O;

B=O, NOH, NOR, NR or S, preferably O or NR and most preferably O;

and where the polysiloxane or the silicone resin is bound to the $(CR_2)_r$(Formula I, II, IV, and V) or $(CR_2)_v$ (Formula III and VI). Any of the linker structures shown in Formulas I through VI can also be interrupted with cycloaliphatic rings or aromatic rings. Substituents on the phenyl group of formulas (IV), (V), and (VI) may be present at any free valence site. The polysiloxanes or silicone resins may or may not contain other functionalities by substitution at silicon atoms either the same as or distinct from those bound to the linking groups described above, such as amine-, polyether-, alkyl-, or heteroalkyl-containing groups.

The linker is typically derived from a polysiloxane or silicone resin bound linker precursor which comprises a linker bound to a leaving group. Illustrative leaving groups include halides such as chloride, bromide and iodide; tosylate, mesylate, phosphate; cyclic leaving groups (that is, those in which the leaving group remains bound in the linker) such as epoxy or other cyclic leaving group containing at least one heteroatom; and other leaving groups known to those skilled in the art. Preferred leaving groups are bromide, chloride, and iodide. In synthesis, the leaving group is replaced by a molecular hook, so that the linker becomes bound to a molecular hook.

The method for making the silicone compositions of the present invention includes combining a molecular hook, a polysiloxane or silicone resin, and a linker. The sequence of addition can be varied, for example, the linker and the molecular hook can be combined and this combination can be sequentially combined with a polysiloxane or a silicone resin. Preferably, the linker is combined with a polysiloxane or silicone resin and the combination is sequentially combined with the molecular hook.

Silicone compositions of the present invention which include at least one polysiloxane or silicone resin, at least one linker, and at least one molecular hook typically impart cosmetic and other durable benefits in products such as hair care products, but also including, textile care products, cosmetic products, oral care products, and animal care products. A particular advantage of the present invention is that the described linkers provide solubility, in consumer relevant media, to the silicone composition as well as the potential for additional hair care benefits which may or may not be typically associated with the functional groups of the linker.

The silicone compositions can be delivered to a substrate, for example hair, in any appropriate formulation, for example water or water and alcohol mixtures which can contain in a range between about 1% by weight and about 99% by weight alcohol based on the total formulation.

In order that those skilled in the art will be better able to practice the invention, the following examples are given by way of illustration and not by way of limitation.

In the following examples, $D^{R1}$ through $D^{R19}$ are defined as:

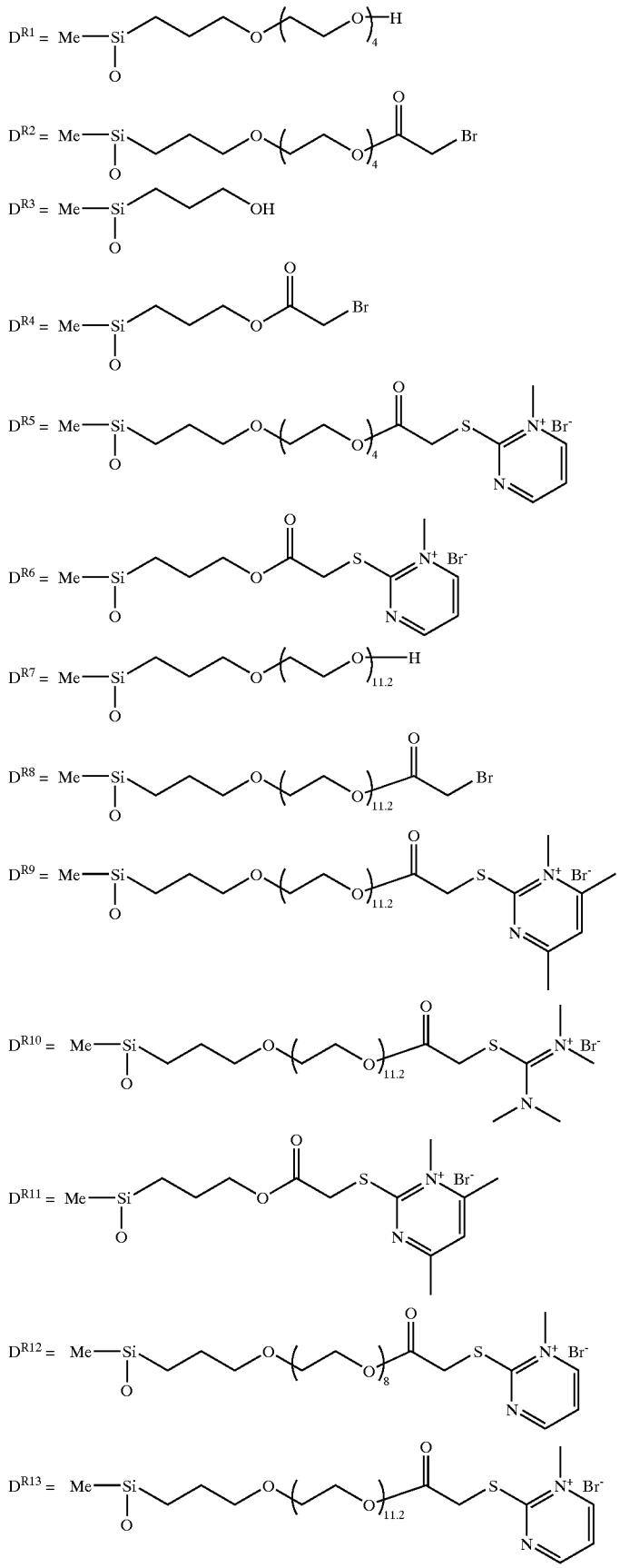

-continued

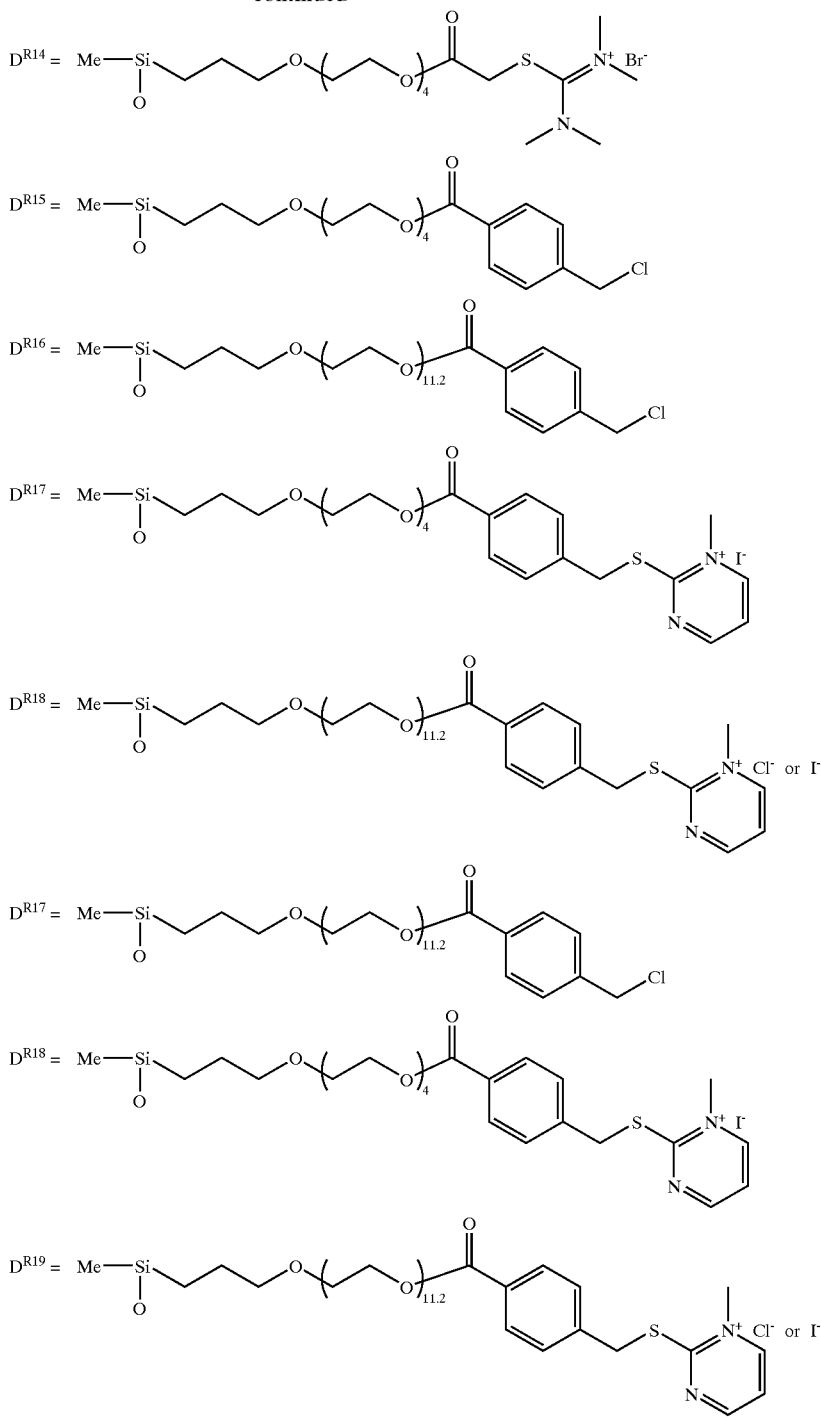

EXAMPLE 1

Silicone hydride fluid ($MD_{21}D^H{}_{3.5}M$). A 1000 milliliter three-neck round bottom flask equipped with a mechanical stirrer, thermometer attached to a temperature controlling device and a drying tube was charged with a silanol terminated polydimethylsiloxane polymer (523.0 grams, 7.07 moles dimethylsiloxy groups), a silicone hydride fluid ($MD^H{}_xM$, 74.50 grams=1.18 moles methylhydridosiloxy groups+0.039 moles trimethylsiloxy groups), hexamethyldisiloxane (51.43 grams, 0.635 moles trimethylsiloxy groups), and a linear phosphonitrilo catalyst (3.23 grams of a 2% solution in the silicone hydride fluid, 100 parts per million). The mixture was stirred at 90° C. for two hours, cooled and then treated with magnesium oxide (1 gram, 0.0256 moles). The mixture was filtered through Celite to furnish the product as a clear, colorless fluid with viscosity of 22.4 centistokes and hydride level of 1892 parts per million. Proton nuclear magnetic resonance spectroscopy ($^1$H NMR) (acetone-$d_6$): δ4.74 (s, 3.5H, SiH), 0.12 (m, 154.5H, SiCH$_3$).

EXAMPLE 2

Silicone hydride fluid ($MD_{48}D^H{}_3M$). A 1000 milliliter three-neck round bottom flask equipped with a mechanical stirrer, thermometer attached to a temperature controlling device and a drying tube was charged with a silanol terminated polydimethylsiloxane polymer (535.1 grams, 7.23 moles dimethylsiloxy groups), a silicone hydride fluid ($MD^H{}_xM$, 30.35 grams=0.48 moles methylhydridosiloxy groups+0.019 moles trimethylsiloxy groups), hexamethyldisiloxane (24.41 grams, 0.3 moles trimethylsiloxy groups) and a linear phosphonitrilo catalyst (2.95 grams of a 2% solution in silicone fluid, 100 parts per million). The mixture was stirred at 90° C. for two hours after which it was cooled and treated with magnesium oxide (1 gram, 0.0256 moles). The mixture was filtered through Celite to furnish the product as a clear, colorless fluid with viscosity of 58.8 centistokes and hydride level of 828 ppm. $^1H$ NMR (acetone-$d_6$): δ4.74 (s, 3.0H, SiH), 0.12 (m, 315.0H, $SiCH_3$).

EXAMPLE 3

Polyether-substituted silicone ($MD_{21}D^{R1}{}_{3.5}M$). A 1000 milliliter three-neck round bottom flask equipped with a stirbar, thermometer attached to a temperature controlling device, addition funnel and a condenser with a drying tube was charged with an allyl-started poly(oxyethylene) ($CH_2CHCH_2O(CH_2CH_2O)_4H$, 157.07 grams, 0.662 moles), 2-propanol (123.4 grams) and Karstedt's catalyst (52 milligrams of a 10% Pt solution in a GE Silicones Product ($M^{Vi}M^{Vi}$) solvent, 8.7 parts per million Pt). The solution was heated to 90° C., and the silicone hydride polymer $MD_{21}D^H{}_{3.5}M$ (317.8 grams, 0.60 moles hydride) was added over 105 minutes. The reaction was followed by gasiometric hydride analysis and was finished within 4 hours after the addition was complete. The 2-propanol was removed at 90° C. in vacuo to provide a light tan silicone polyether fluid with viscosity of about 200 centistokes. $^1H$ NMR (acetone-$d_6$): δ3.85 (m, 7.0H, $CH_2CH_2OH$), 3.74 (m, 7.0H, $CH_2CH_2OH$), 3.57 (s, 56.0H, $OCH_2CH_2O$), 3.41 (m, 7.0H, $SiCH_2CH_2CH_2O$), 1.63 (m, 7.0H, $SiCH_2CH_2CH_2O$), 0.58 (m, 7.0H, $SiCH_2CH_2CH_2O$), 0.12 (m, 154.5H, $SiCH_3$).

EXAMPLE 4

Silicone with bromo-acetylated polyether substituents ($MD_{21}D^{R2}{}_{3.5}M$). A 250 milliliter three-neck round bottom flask equipped with a stirbar, thermometer attached to a temperature controlling device, Dean-Stark trap with a condenser and a drying tube was charged with bromoacetic acid (22.35 grams, 0.161 moles), Isopar C (Exxon Product)(40.0 grams), and the silicone polyether fluid $MD_{21}D^{R1}{}_{3.5}M$ (133.85 grams, 0.169 equivalents hydroxy groups). The reaction mixture was sparged with nitrogen for 20 minutes at ambient temperature to remove dissolved air. para-Toluenesulfonic acid (1.89 grams, 11 millimoles) was added, and the reaction mixture was heated to 100° C. Water and Isopar C were collected in the Dean-Stark trap. After two hours, 94% of the theoretical amount of water was obtained (2.73 grams) and the reaction mixture was cooled to ambient conditions. Potassium carbonate (3.80 grams, 27.6 millimoles) was added to neutralize the reaction and the salts were removed by filtration through Celite after at least two hours of stirring. $^1H$ NMR (acetone-$d_6$): δ4.27 (m, 7.0H, $CH_2CH_2OC(O)$), 4.03 (s, 7.0H, $CH_2Br$), 3.70 (m, 7.0H, $OCH_2CH_2OC(O)$), 3.57 (s, 56.0H, $OCH_2CH_2O$), 3.41 (m, 7.0H, $SiCH_2CH_2CH_2O$), 1.63 (m, 7.0H, $SiCH_2CH_2CH_2O$), 0.58 (m, 7.0H, $SiCH_2CH_2CH_2O$), 0.12 (m, 154.5H, $SiCH_3$).

EXAMPLE 5

Hydroxypropyl-substituted silicone ($MD_{45}D^{R3}{}_{3.5}M$). A 2000 milliliter three-neck round bottom flask equipped with a stirbar, thermometer attached to a temperature controlling device, addition funnel, and a condenser with a drying tube was charged with allyl alcohol (76.0 milliliters, 64.90 grams, 1.12 moles), 2-propanol (160 grains), and Karstedt's catalyst (706.8 mg of a 1% Pt solution in 2-propanol, 11 parts per million Pt). The solution was heated to reflux (85° C.) and the silicone hydride polymer ($MD_{45}D^H{}_{3.5}M$, 600 grams, 0.557 moles hydride) was added over 120 minutes. The reaction was followed by gasiometric hydride analysis and was finished within 6 hours after the addition was complete. The 2-propanol was removed at 90° C. in vacuo to provide a light tan silicone polyether fluid with viscosity of 170 centistokes. $^1H$ NMR (acetone-$d_6$): δ3.50 (t, 7.0H, $SiCH_2CH_2CH_2OH$), 1.60 (m, 7.0H, $SiCH_2CH_2CH_2O$), 0.58 (m, 7.0H, $SiCH_2CH_2CH_2O$), 0.12 (m, 298.5H,

EXAMPLE 6

Silicone with bromo-acetylated propyl substituents ($MD_{45}D^{R4}{}_{3.5}M$). A 500 milliliter three-neck round bottom flask equipped with a stirbar, thermometer attached to a temperature controlling device, Dean-Stark trap with a condenser and a drying tube was charged with bromoacetic acid (35.42 grams, 0.255 moles), Isopar C (280 grams), and the hydroxypropyl-substituted silicone fluid ($MD_{45}D^{R3}{}_{3.5}M$, 300.0 grams, 0.268 equivalents hydroxy groups). The reaction mixture was sparged with nitrogen for 30 minutes at ambient temperature to remove the dissolved air. para-Toluenesulfonic acid (2.50 grams, 13.1 millimoles) was added and the reaction mixture was heated to 100° C. Water and Isopar C were collected in the Dean-Stark trap. After two hours, the theoretical amount of water was obtained (4.1 grams), and the reaction mixture was cooled to ambient conditions. Excess sodium carbonate was added to neutralize the reaction, and the salts were removed by filtration through Celite after at least two hours of stirring. The volatile materials were removed under vacuum to give 324.2 grams of product (98% yield). $^1H$ NMR (acetone-$d_6$): δ4.12 (t, 7.0H, $CH_2CH_2OC(O)$), 3.99 (s, 7.0H, $CH_2Br$), 1.76 (m, 7.0H, $SiCH_2CH_2CH_2O$), 0.63 (m, 7.0H, $SiCH_2CH_2CH_2O$), 0.12 (m, 298.5H, $SiCH_3$).

EXAMPLE 7

Pyrimidinium-substituted polyether silicone ($MD_{21}D^{R5}{}_{3.5}M$). A 250 milliliter round bottom flask containing a stir bar was charged with 37.50 grams (11.19 millimoles) of the silicone polyether fluid $MD_{21}D^{R2}{}_{3.5}M$, followed by approximately 30 milliliters of acetonitrile. 1-Methyl-2(1H)-pyrimidinethione (5.141 grams, 40.74 millimoles) was added in proportions as a solid with another 30 milliliters of acetonitrile. The dark brown, heterogeneous solution was allowed to stir at room temperature, and after about one hour, the reaction mixture became a completely homogeneous yellowish-brown solution. The reaction continued to stir for approximately 16 hours and became a brown-yellow cloudy mixture. Later experiments revealed that the reaction goes to completion in approximately 2.5 hours. The volatile materials were removed under vacuum to yield a clear, dark orange, waxy solid in 85.2% yield (33.30 grams). $^1H$ NMR (acetone-$d_6$): δ10.16 (s, 3.5H, pyH), 9.33 (m, 3.5H, pyH), 8.04 (m, 3.5H, pyH), 4.49 (m, 17.5H, $NCH_3+CH_2CH_2OC(O)$), 4.30 (s, 7.0H, $CH_2S$), 3.68 (t, 7.0H, $CH_2OCH_2CH_2OC(O)$), 3.59 (m, 42.0H, $OCH_2CH_2O$), 3.41 (t, 7.0H, $SiCH_2CH_2CH_2O$), 1.64 (m, 7.0H, $SiCH_2CH_2CH_2O$), 0.58 (m, 7.0H, $SiCH_2CH_2CH_2O$), 0.12 (s, 136.5H, $SiCH_3$).

EXAMPLE 8

Pyrimidinium-substituted silicone ($MD_{45}D^{R6}{}_{3.5}M$). The polymer $MD_{45}D^{R4}{}_{3.5}M$ (39.18 grams, 29.79 millimoles bromide) was added together with a stir bar to a three-neck 250 milliliter round bottom flask fitted with a condenser (with an $N_2$ adapter on top) and 2 rubber septa. The silicone was sparged with nitrogen for 10 minutes after which 1-methyl-2(1H)-pyrimidinethione (3.382 grams, 26.80 millimoles) was added as a solid under a nitrogen flow. An equal volume amount of acetonitrile was added, and the mixture was sparged with $N_2$ for an additional 15 min. The mixture was vigorously stirred at 55° C. for 17.5 hours under nitrogen. The cloudy orange $CH_3CN$ layer was decanted from the cloudy orange silicone layer. The silicone layer was washed with an equal volume of $CH_3CN$ two times. The product was dried under vacuum yielding 32.29 grams (75.2%) of a light orange rubber-like solid. $^1H$ NMR (acetone-$d_6$): δ10.16 (br s, 3H, pyH), 9.27 (br s, 3H, pyH), 8.04 (br s, 3H, pyH), 4.49 (s, 15H, $CH_2S+NCH_3$), 4.16 (t, 6H, $CH_2O$), 1.77 (m, 6H, $CH_2CH_2CH_2$, 6H), 0.62 (m, 6H, $SiCH_2$), 0.12 (s, 297H, $SiCH_3$).

EXAMPLE 9

Polyether-substituted silicone polymer ($MD_{52.7}D^{R7}{}_{3.3}M$). A 1000 milliliter three-neck round bottom flask equipped with a stirbar, thermometer attached to a temperature controlling device, addition funnel and a condenser with a drying tube was charged with an allyl-started poly (oxyethylene) (176.47 grams, 0.329 moles), 2-propanol (119.0 grams) and Karstedt's catalyst (86.6 milligrams of a 10% Pt solution using a GE Silicones $M^{Vi}M^{Vi}$ product as solvent). The solution was heated to 88° C. and the silicone hydride polymer $MD_{52.7}D^{H}{}_{3.3}M$ (300.0 grams, 0.2917 moles hydride, prepared by the same method as described above) was added over 90 minutes. The reaction was followed by gasiometric hydride analysis and was finished within 4 hours after the addition was complete. The volatile materials including 2-propanol were removed at 90° C. under vacuum to provide a light tan silicone polyether fluid with viscosity of 1336 centistokes. $^1H$ NMR (acetone-$d_6$): δ3.85 (m, 6.6H, $CH_2CH_2OH$), 3.74 (m, 6.6H, $CH_2CH_2OH$), 3.57 (s, 132.7H, $OCH_2CH_2O$), 3.41 (m, 6.6H, $SiCH_2CH_2CH_2O$), 1.63 (m, 6.6H, $SiCH_2CH_2CH_2O$), 0.58 (m, 6.6H, $SiCH_2CH_2CH_2O$), 0.12 (m, 344.1H, $SiCH_3$).

EXAMPLE 10

Silicone polymer with bromo-acetylated polyether substituents ($MD_{52.7}D^{R8}{}_{3.3}M$). A 1000 milliliter three-neck round bottom flask equipped with a stirbar, thermometer attached to a temperature controlling device and a Dean-Stark trap with a condenser and a drying tube was charged with bromoacetic acid (34.00 grams, 0.245 moles), Isopar C (314 grams) and the polyether-substituted silicone $MD_{52.7}D^{R7}{}_{3.3}M$ (397.5 grams, 0.257 equivalents hydroxy groups). The reaction mixture was sparged with nitrogen for 20 minutes at ambient temperature to remove the dissolved air. para-Toluenesulfonic acid (2.36 grams, 13.7 millimoles) was added, and the reaction mixture was heated to 100° C. Water and Isopar C were collected in the Dean-Stark trap. After two hours, 98% of the theoretical amount of water was obtained (4.4 grams), and the reaction mixture was cooled to ambient conditions. Potassium carbonate (3.80 grams, 27.6 millimoles) was added to neutralize the reaction, and the salts were removed by filtration through Celite after at least two hours of stirring to yield a product with viscosity of 1843 centistokes. $^1H$ NMR (acetone-$d_6$): δ4.27 (m, 6.6H, $CH_2CH_2OC(O)$), 4.04 (s, 6.6H, $CH_2Br$), 3.70 (m, 6.6H, $OCH_2CH_2OC(O)$), 3.58 (s, 132.7H, $OCH_2CH_2O$), 3.41 (m, 6.6H, $SiCH_2CH_2CH_2O$), 1.63 (m, 6.6H, $SiCH_2CH_2CH_2O$), 0.58 (m, 6.6H, $SiCH_2CH_2CH_2O$), 0.12 (m, 344.1H, $SiCH_3$).

EXAMPLE 11

Trimethylpyrimidinium-substituted polyether silicone polymer ($MD_{53}D^{R9}{}_{3.3}M$). A flask was charged with 33.5 g (5.53 millimoles) of the silicone polymer $MD_{53}D^{R8}{}_{3.3}M$. Acetone (50 milliliters) was added followed by 2.90 g of 1,4,6-trimethyl-pyrimidine-2-thione (22.7 millimoles). The suspension was allowed to stir for 1.5 h, after which 0.08 mole percent of excess thione remained by $^1H$ NMR spectroscopy. After the addition of 1.97 grams (0.325 millimoles) more silicone polymer, the mixture was left stirring overnight. The mixture was then centrifuged to remove the solid salts remaining, and the product solution was decanted. The volatile materials were removed under vacuum affording 32.6 grams (86% yield) of polymer product. $^1H$ NMR (acetone-d6): δ7.96 (m, 3.5H, pyH), 4.38 (s, 7.0H., $CH_2$s), 4.26 (m, 17.5H, $NCH_3$, $OCH_2CH_2OC(O)$), 3.70 (m, 7H, $CH_2OCH_2CH_2OC(O)$), 3.58 (m, 142.8H, $OCH_2CH_2O$), 3.39 (t, 7.0H, $SiCH_2CH_2CH_2O$), 3.00 (s, 7H, py$CH_3$), 2.68 (s, 7H, py$CH_3$), 1.62 (m, 7.0H, $SiCH_2CH_2CH_2O$), 0.58 (m, 7.0H, $SiCH_2CH_2CH_2O$), 0.12 (s, 344H, $SiCH_3$).

EXAMPLE 12

1,1,3,3-Tetramethyl-2-thiuronium-substituted polyether silicone ($MD_{53}D^{R10}{}_{3.3}M$). A 300 milliliter round bottom flask containing a stir bar was charged with 35.47 g (5.446 millimoles) of the polyether-substituted silicone polymer $MD_{52.7}D^{R8}{}_{3.3}M$ followed by approximately 40 milliliters of acetonitrile. 1,1,3,3-Tetramethyl-2-thiourea (2.262 grams, 17.11 millimoles) was added in portions as a solid followed by another 30 milliliters of acetonitrile. After stirring overnight at room temperature, the cloudy, light yellow solution became clear and pale yellow.

The volatile materials were removed under vacuum, and the final product was recovered in 99.4% yield as a clear, pale yellow, gooey solid. $^1H$ NMR (acetone-d6): δ4.31 (t, 6.6H, $CH_2CH_2OC(O)$), 4.20 (s, 6.6, $CH_2S$), 3.73 (t, 6.6H, $CH_2OCH_2CH_2OC(O)$), 3.59 (m, 33.66H, $OCH_2CH_2O$), 3.48, (s, 36.0, $N(Me)_2$), 3.41 (t, 6.6H, $SiCH_2CH_2CH_2O$), 1.64 (m, 6.6H, $SiCH_2CH_2CH_2O$), 0.58 (m, 6.6H $SiCH_2CH_2CH_2O$), 0.12 (s, 345.6H, $SiCH_3$).

EXAMPLE 13

Trimethylpyrimidinium-substituted silicone polymer ($MD_{45}D^{R11}{}_{3.5}M$). A flask was charged with 35.0 grams (8.0 millimoles) of the silicone polymer $MD_{45}D^{R4}{}_{3.5}M$ followed by 50 milliliters of acetone. Following the addition of 3.54 grams of 1,4,6-trimethyl-pyrimidine-2-thione (22.7 millimoles), the suspension was left stirring for six hours, whereupon starting material still remained by $^1H$ NMR. After the addition of four mole percent additional thione, the mixture was left stirring overnight. The following morning, the mixture was centrifuged to remove the solid salts remaining, and the product solution was decanted and concentrated, affording 37.8 grams (87% yield) of polymer product. $^1H$ NMR (acetone-$d_6$): δ8.03 (m, 3.5H, pyH), 4.39 (s, 7.0H, $CH_2S$), 4.26 (m, 10.5H, $NCH_3$, 4.14 (t, 7.0H, $CH_2CH_2CH_2OC(O)$), 3.02 (s, 7.0H, py$CH_3$), 2.67 (s, 7.0H, py$CH3$), 1.78 (m, 7.0H, $CH_2CH_2CH_2OC(O)$), 0.63 (t, 7.0H, $CH_2CH_2CH_2OC(O)$), 0.12 (m, 297H, $SiCH_3$)

EXAMPLES 14–19

Using the same procedures as described above for the structurally analogous polymers, the following materials were also synthesized:

$MD_{45}D^{R5}{}_3M$
$MD_{21}D^{R12}{}_3M$
$MD_{19}D^{R8}{}_5M$
$MD_{45}D^{R13}{}_3M$
$MD_{32}D^{R6}{}_3M$
$MD_{21}D^{R14}{}_3M$

It should be noted that while most reactions in which cationic polymers were made were performed at room temperature, in most instances they can be heated to speed the reaction.

Silicone deposition. Polymers described in this invention impart durable benefits to hair such as good combability, manageability, etc. The degree to which the new silicone materials interact with hair durably, after repeated shampooing of hair switches with commercially available shampoo (Prell®), was measured. Permed, bleached, and colored hair switches were contacted with ethanol/water mixtures containing the silicone polymer $MD_{21}D^{R5}{}_{3.5}M$ (5% by weight). All experiments were performed with water at pH 9.5 (not buffered). Hair switches were rinsed, extracted, and shampooed 20 times. They were then analyzed for silicon by x-ray fluorescence (XRF). The counts were converted to ppm silicon deposition using standard methods.

TABLE 1

XRF data collected on hair switches treated with new silicone polymers after extraction and 20 shampoos with Prell ®.

| Switches | Polymer | Solvent (EtOH/ water) | pH | Treatment Time (min) | Silicone Deposition (ppm)[2] |
|---|---|---|---|---|---|
| 1–3 | $MD_{45}D^{R6}{}_{3.5}M$ | 90/10 | 7 | 5 | 954 |
| 4–6 | $MD_{45}D^{R6}{}_{3.5}M$ | 90/10 | 7 | 30 | 2574 |
| 7–9 | $MD_{45}D^{R6}{}_{3.5}M$ | 90/10 | 7 | 60 | 1836 |
| 10–12 | $MD_{45}D^{R6}{}_{3.5}M$ | 90/10 | 9.5 | 30 | 5642 |
| 13–15 | $MD_{45}D^{R6}{}_{3.5}M$ | 20/80 | 9.5 | 30 | 2868 |
| 16–18 | $MD_{45}D^{R11}{}_{3.5}M$ | 90/10 | 7 | 5 | 951 |
| 19–21 | $MD_{45}D^{R11}{}_{3.5}M$ | 90/10 |  | 30 | 1349 |
| 22–24 | $MD_{45}D^{R11}{}_{3.5}M$ | 90/10 | 9.5 | 5 | 2619 |
| 25–27 | $MD_{45}D^{R11}{}_{3.5}M$ | 90/10 | 9.5 | 30 | 3281 |
| 28–30 | $MD_{45}D^{R11}{}_{3.5}M$ | 90/10 (buffered)[2] | 9.5 | 30 | 9254 |
| 31–33 | $MD_{32}D^{R6}{}_3M$ | 90/10 | 7 | 30 | 3408 |
| 34–36 | $MD_{32}D^{R6}{}_3M$ | 90/10 | 9.5 | 30 | 6682 |
| 37–39 | $MD_{32}D^{R6}{}_3M$ | 20/80 | 7 | 30 | 1891 |
| 40–42 | $MD_{32}D^{R6}{}_3M$ | 20/80 | 9.5 | 30 | 4500 |
| 43–45 | $MD_{32}D^{R6}{}_3M$ | 20/80 | 9.5 | 5 | 3268 |
| 46–48 | $MD_{32}D^{R6}{}_3M$ | 20/80 | 9.5 | 60 | 2759 |
| 49–51 | $MD_{21}D^{R14}{}_3M$ | 90/10 | 7 | 10 | 432 |
| 52–54 | $MD_{21}D^{R14}{}_3M$ | 90/10 | 7 | 60 | 673 |
| 55–57 | $MD_{21}D^{R14}{}_3M$ | 90/10 | 7 | 120 | 1759 |
| 58–60 | $MD_{21}D^{R14}{}_3M$ | 90/10 | 9.5 | 30 | 678 |
| 61–63 | $MD_{21}D^{R14}{}_3M$ | 90/10 | 9.5 | 60 | 1639 |

[1]Reported values are the average of measurements taken on three different hair switches treated under the same conditions.
[2]Amino methylpropanol.

Control experiments of hair switches treated with a polysiloxane without the linker and molecular hook (polydimethylsiloxane with a viscosity of 350 centistokes) for 5 minutes showed an initial deposition level of silicon as 2050 parts per million by XRF. Measurements showed that after 8 shampoos, no silicone remained on the hair. Unfunctionalized polysiloxanes or silicone resins are known to show very limited durability. The data in Table 1 clearly show that the new silicone polymers which provide conditioning benefits do adhere to the hair with unexpected durability.

EXAMPLE 20

Silicone hydride fluid ($MD_{21}D^{H}{}_{3.5}M$). A 1000 milliliter three-neck round bottom flask equipped with a mechanical stirrer, thermometer attached to a temperature controlling device and a drying tube was charged with a silanol terminated polydimethylsiloxane polymer (523.0 grams, 7.07 moles dimethylsiloxy groups), a silicone hydride fluid ($MD^{H}{}_xM$, 74.50 grams=1.18 moles methylhydridosiloxy groups+0.039 moles trimethylsilyoxy groups), hexamethyldisiloxane (51.43 grams, 0.635 moles trimethylsilyoxy groups), and a linear phosphonitrilo catalyst (3.23 grams of a 2% solution in silicone fluid, 100 parts per million). The mixture was stirred at 90° C. for two hours, cooled and then treated with magnesium oxide (1 gram, 0.0256 moles). The mixture was filtered through Celite to furnish the product as a clear, colorless fluid with viscosity of 22.4 centistokes and hydride level of 1892 parts per million. $^1H$ NMR (acetone-$d_6$): δ4.74 (s, 3.5H, SiH), 0.12 (m, 154.5H, $SiCH_3$).

EXAMPLE 21

Polyether-substituted silicone ($MD_{21}D^{R1}{}_{3.5}M$). A 1000 milliliter three-neck round bottom flask equipped with a stirbar, thermometer attached to a temperature controlling device, addition funnel and a condenser with a drying tube was charged with an allyl-started poly(oxyethylene) ($CH_2CHCH_2O(CH_2CH_2O)_4H$, 157.07 grams, 0.662 moles), 2-propanol (123.4 grams) and Karstedt's catalyst (52 mg of a 10% Pt solution, 8.7 parts per million Pt in a GE Silicones $M^{Vi}M^{Vi}$ solvent). The solution was heated to 90° C., and the silicone hydride polymer $MD_{21}D^{H}{}_{3.5}M$ (317.75 grams, 0.60 moles hydride) was added over 105 minutes. The reaction was followed by gasiometric hydride analysis and was finished within 4 hours after the addition was complete. The 2-propanol was removed at 90° C. in vacuo to provide a light tan silicone polyether fluid with viscosity of about 200 centistokes. $^1H$ NMR (acetone-$d_6$): δ3.85 (m, 7.0H, $CH_2CH_2OH$), 3.74 (m, 7.0H, $CH_2CH_2OH$), 3.57 (s, 56.0H, $OCH_2CH_2O$), 3.41 (m, 7.0H, $SiCH_2CH_2CH_2O$), 1.63 (m, 7.0H, $SiCH_2CH_2CH_2O$), 0.58 (m, 7.0H, $SiCH_2CH_2CH_2O$), 0.12 (m, 154.5H, $SiCH_3$).

EXAMPLE 22

Polyether-substituted silicone polymer ($MD_{52.7}D^{R7}{}_{3.3}M$). A 1000 milliliter three-neck round bottom flask equipped with a stirbar, thermometer attached to a temperature controlling device, addition funnel and a condenser with a drying tube was charged with an allyl-started poly (oxyethylene) (176.47 grams, 0.329 moles), 2-propanol (119.0 grams) and Karstedt's catalyst (86.6 mg of a 10% Pt solution in a GE Silicone Products $M^{Vi}M^{Vi}$ solvent). The solution was heated to 88° C., and the silicone hydride polymer $MD_{52.7}D^{H}{}_{3.3}M$ (300.0 grams, 0.2917 moles hydride), prepared by the same method as described above, was added over 90 minutes. The reaction was followed by gasiometric hydride analysis and was finished within 4 hours after the addition was complete. The volatile materials including 2-propanol were removed at 90° C. under vacuum to provide a light tan silicone polyether fluid with viscosity of 1336 centistokes. $^1H$ NMR (acetone-$d_6$): δ3.85 (m, 6.6H, $CH_2CH_2OH$), 3.74 (m, 6.6H, $CH_2CH_2OH$), 3.57 (s, 132.7H, $OCH_2CH_2O$), 3.41 (m, 6.6H, $SiCH_2CH_2CH_2O$), 1.63 (m, 6.6H, $SiCH_2CH_2CH_2O$), 0.58 (m, 6.6H, $SiCH_2CH_2CH_2O$), 0.12 (m, 334.1H, $SiCH_3$).

EXAMPLE 23

Benzylchloride-substituted polyether silicone ($MD_{21}D^{R15}{}_{3.5}M$). A 500 milliliter three-neck flask equipped with thermometer, drying tube and stirbar was charged with the silicone polyether $MD_{21}D^{R1}{}_{3.5}M$ (66.58 grams, 0.0889 moles OH), diethyl ether (35 milliliters) and triethylamine (9.242 g, 0.0915 moles). The reaction mixture was cooled with an ice bath to 5° C. A solution of 4-chloromethylbenzoyl chloride (15 grams, 0.0794 moles) in diethyl ether (30 milliliters) was added over 28 minutes, keeping the reaction temperature below 20° C. After 15 minutes the bath was removed, and the reaction was warmed to ambient temperature. After one hour more, the triethylammonium salt was filtered off and washed with fresh diethyl ether, and the filtrate was concentrated on a rotary evaporator to a viscous fluid. The product was then dried under vacuum to afford 73.63 grams (93.5% yield of polymer product). $^1$H NMR (acetone-$d_6$): $\delta$8.02 (7H, d, ArH), 7.57 (7H, d, ArH), 4.78 (7H, s, $CH_2Cl$), 4.43 (7H, t, $CH_2OC=O$), 3.82 (7H, t, $OCH_2CH_2OC=O$), 3.55 (42H, m, $OCH_2CH_2O$), 3.40 (7H, t, $OCH_2CH_2CH_2Si$), 1.63 (7H, m, $OCH_2CH_2CH_2Si$), 0.58 (7H, m, $OCH_2CH_2CH_2Si$), and 0.12 (154.5H, m, $SiCH_3$).

EXAMPLE 24

Benzylchloride-substituted polyether silicone ($MD_{45}D^{R16}_3M$). A 500 milliliter three-neck round bottom flask was charged with 154.7 grams (29.03 millimoles) of the carbinol-terminated silicone polymer $MD_{45}D^{R2}_3M$ and 175 milliliters of anhydrous diethyl ether. After the addition of 8.37 g (82.72 millimoles) of triethylamine, the mixture was cooled to 5° C. under nitrogen. An addition funnel was charged with 15.64 g (82.72 millimoles) of 4-chloromethylbenzoyl chloride dissolved in 10 milliliters of diethylether. This solution was added dropwise to the stirring polymer solution held at 5° C. over a ten minute period. After one hour the ice bath was removed, and the reaction was warmed to room temperature overnight. The next morning the mixture was filtered through Celite to remove the salt. The filtrate was diluted with hexanes, whereupon more triethylamine salt precipitated. The mixture was filtered again, concentrated and dried under vacuum to afford 154.2 grams (92% yield) of polymer product. $^1$H NMR (acetone-$d_6$): $\delta$8.01 (d, 6H, ArH), 7.57 (d, 6H, ArH), 4.83 (s, 6H, $CH_2Cl$), 4.47 (t, 6H, $CH_2OCH_2CH_2OC(O)$), 3.79 (t, 6H, $CH_2OCH_2CH_2OC(O)$), 3.58 (m, 122.4H, $OCH_2CH_2O$), 3.39 (t, 6.0H, $SiCH_2CH_2CH_2O$), 1.59 (m, 6.0H, $SiCH_2CH_2CH_2O$), 0.60 (m, 6.0H, $SiCH_2CH_2CH_2O$), 0.11 (s, 297H, $SiCH_3$).

EXAMPLE 25

Pyrimidinium-substituted polyether silicone ($MD_{21}D^{R17}_{3.5}M$). A 250 milliliter round bottom flask containing a stir bar was charged with 20.61 grams (7.282 millimoles) of the silicone polyether fluid $MD_{21}D^{R15}_{3.5}M$ followed by approximately 15 milliliters of acetone. Sodium iodide (3.272 g, 21.83 millimoles) was added in portions as a solid, followed by approximately 10 milliliters of acetone, 2.741 grams (21.72 millimoles) of 1-methyl-2(1H)-pyrimidinethione, and another 25 milliliters of acetone. The orange-yellow heterogeneous solution, which gradually turned orange-red, was allowed to stir at room temperature for one day. The liquid was decanted from the white precipitate, and the solid was washed twice with an equal volume of acetone. The decanted solution and washings were combined and dried using a rotary evaporator. The final product was recovered upon drying under vacuum as a viscous material in 98.6% yield (25.01 grams). $^1$H NMR (acetone-$d_6$): $\delta$9.71 (s, 3.5H, pyH), 9.39 (s, 3.5H, pyH), 8.02 (m, 3.5H, pyH), 7.97 (m, 7H, aryl), 7.77 (d, 7H, aryl), 4.95 (s, 7H, $CH_2S$), 4.42 (t, 7H, $CH_2CH_2OC(O)$), 4.36 (s, 10.5H, NMe), 3.81 (t, 7H, $CH_2CH_2OC(O)$), 3.56 (m, 42H, $OCH_2CH_2O$), 3.40 (t, 7.0H, $SiCH_2CH_2CH_2O$), 1.63 (m, 6.0H, $SiCH_2CH_2CH_2O$), 0.58 (m, 6.0H, $SiCH_2CH_2CH_2O$), 0.12 (s, 154.5H, $SiCH_3$).

EXAMPLE 26

Pyrimidinium-substituted polyether silicone ($MD_{45}D^{R18}_3M$). A 500 milliliter round bottom flask was charged with 130.5 g (22.54 millimoles) of $MD_{45}D^{R16}_3M$. Following the addition of 7.94 grams (62.9 millimoles) 1-methyl-2(1H)-pyrimidinethione, 1.014 grams (6.76 millimoles) of sodium iodide and 125 milliliters of acetonitrile, the suspension was stirred, protected from light, overnight at room temperature. The next morning, an additional 10 mole percent of thione was added due to incomplete reaction as determined by $^1$H NMR spectroscopy. After a period of four days and the addition of an additional 50 mole percent of sodium iodide, the reaction was complete by 1H NMR spectroscopy. The volatile materials were removed under vacuum, and the polymer was dissolved in acetone. The mixture was filtered through Celite to remove the salts. The volatile materials were then removed under vacuum to afford 136 g of polymer product. $^1$H NMR (acetone-$d_6$): $\delta$9.71 (s, 3H, pyH), 9.39 (s, 3H, pyH), 8.12 (s, 3H, pyH), 7.97(d, 6H, ArH), 7.77 (d, 6H, ArH), 5.00 (s, 6H, $CH_2S$), 4.43 (t, 6H, $CH_2OCH_2CH_2OC(O)$), 4.33 (m, 9H, $NCH_3$), 3.79 (t, 6H, $CH_2OCH_2CH_2OC(O)$), 3.58 (m, 122.4H, $OCH_2CH_2O$), 3.39 (t, 6.0H, $SiCH_2CH_2CH_2O$), 1.61 (m, 6.0H, $SiCH_2CH_2CH_2O$), 0.59 (m, 6.0H, $SiCH_2CH_2CH_2O$), 0.12 (s, 297H, SiMe).

As with Examples 1–19, it should be noted that while most reactions in which cationic polymers were made were performed at room temperature, in most instances they can be heated to speed the reaction.

Silicone deposition. The polymers described in this invention impart durable benefits to hair such as good combability, manageability, etc. The degree to which the new silicone materials interact with hair durably, after repeated shampooing, was measured. Permed, bleached and colored hair switches were contacted with ethanol/water mixtures containing the silicone polymer $MD_{21}D^{R17}_{3.5}M$ (5% by weight, see Table 2). All experiments were performed with water at pH 9.5 (not buffered). Following treatment, the hair switches were rinsed, extracted and washed with a commercially available shampoo (Prell®) 20 times. They were then analyzed for silicon by x-ray fluorescence (XRF). The counts were converted to ppm silicon deposition using standard methods.

TABLE 2

XRF data collected on hair switches treated with $MD_{21}D^{R17}_{3.5}M$ after extraction and 20 shampoos.

| Switches | Solvent (EtOH/water) | Treatment Time (min) | Silicone Deposition (ppm)[1] |
| --- | --- | --- | --- |
| 64–66 | 90/10 | 30 | 3286 |
| 67–69 | 90/10 | 60 | 3754 |
| 70–72 | 20/80 | 5 | 481 |
| 73–75 | 20/80 | 30 | 922 |
| 76–78 | 20/80 | 60 | 1538 |

[1]Reported values are the average of measurements taken on three different hair switches treated under the same conditions.

Control experiments of hair switches treated with a polysiloxane without the linker and molecular hook (polydimethylsiloxane with a viscosity of 350 centistokes) for 5 minutes showed an initial deposition level of silicon as 2050 parts per million by XRF. Measurements showed that after 8 shampoos, no silicone remained on the hair. The data in Table 2 clearly show that the new silicone polymers which provide conditioning benefits do adhere to the hair with unexpected durability.

Hair care benefits. Sensory testing confirmed that remarkable durable benefits are delivered by the new silicone polymers. For example, trained panelists found that highly damaged doubly colored hair treated briefly with $MD_{21}D^{R17}_{3.5}M$ exhibited superior wet combing and wet feel properties compared to uncolored virgin hair even after 36 washes. Treatment with the new polymer improved other properties such as dry combing, dry feel, volume, clean feel and shine to the point where they were equivalent to uncolored virgin hair. In these experiments, the doubly colored hair was washed 8 times with Prell® shampoo between colorings. The hair was treated with a 90/10 ethanol/water mixture containing $MD_{21}D^{R17}_{3.5}M$ (3% by weight) for 5 minutes at pH 9.5 (not buffered). The benefits were assessed by the panelists periodically through 36 washes with Pantene® shampoo (no conditioner). The uncolored virgin hair controlled was also washed with Pantene® shampoo for the same number of cycles.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A silicone composition which comprises at least one polysiloxane or silicone resin, at least one molecular hook, and at least one linker wherein the linker comprises at least one moiety of the formulas (I), (II), (III), (IV), (V), or (VI):

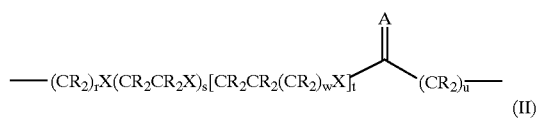
(I)

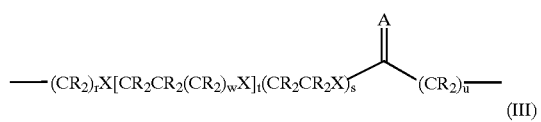
(II)

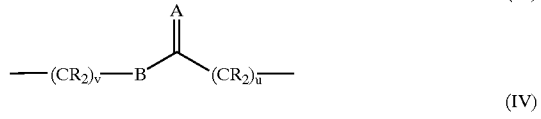
(III)

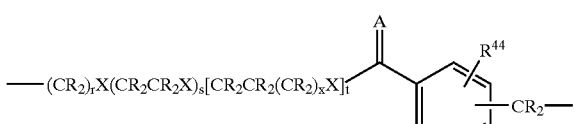
(IV)

(V)

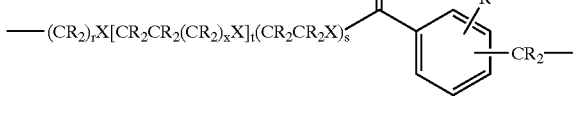
(VI)

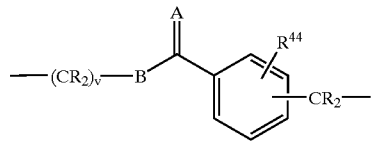

wherein r is in a range between about 1 and about 10;
wherein s is in a range between about 0 and about 100;
wherein t is in a range between about 0 and about 100;
wherein u is in a range between about 1 and about 10;
wherein v is in a range between about 1 and about 10;
wherein w is 1 or 2;
wherein x is 1 or 2;
wherein X is O, NOH, NOR, or NR;
wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the C can be unsubstituted or substituted with heteroatoms such as oxygen (O), nitrogen (N), sulfur (S) or halogen;
wherein $R^{44}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen;
A=O, NOH, NOR, NR or S;
B=O, NOH, NOR, NR or S;
and where the polysiloxane or the silicone resin is bound to the $(CR_2)_r$ (Formula I, II, IV, and V) or $(CR_2)_v$ (Formula III and VI).

2. The composition in accordance with claim 1, wherein r is 2 or 3; s is in a range between about 4 and about 20; t is 0; u is 1; v is 2 or 3; w is 1 or 2; x is 1 or 2; X is O; R is H; $R^{44}$ is H; A is O; and B is O.

3. The composition in accordance with claim 1, wherein the at least one linker is bound to a polysiloxane or silicone resin through a silicon, carbon, oxygen, nitrogen, or sulfur atom.

4. The composition in accordance with claim 3, wherein the at least one linker is bound to a polysiloxane or silicone resin through a silicon atom.

5. The composition in accordance with claim 1, having the formula $$M_a M'_b D_c D'_d T_e T'_f Q_g$$

where the subscripts a, b, c, d, e, f and g are zero or a positive integer, subject to the limitation that the sum of the subscripts b, d and f is one or greater; where M has the formula:

M' has the formula:

D has the formula:

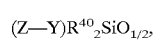

D' has the formula:

T has the formula:

T' has the formula:

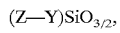

and Q has the formula $SiO_{4/2}$, where each $R^{39}$, $R^{40}$, $R^{41}$, $R^{42}$, $R^{43}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; each Z, independently at each occurrence, is a molecular hook; and each Y, independently at each occurrence, is a linker.

6. The composition of claim 5 in which the average number of Y—Z moieties on a polysiloxane or silicone resin is between about 1 and about 100.

7. The composition of claim 5 in which the average number of Y—Z moieties on a polysiloxane or silicone resin is between about 1 and about 10.

8. The composition of claim 5 comprising at least one compound of the following formulas, (VII), (VIII), (IX), (X), (XI), or (XII):

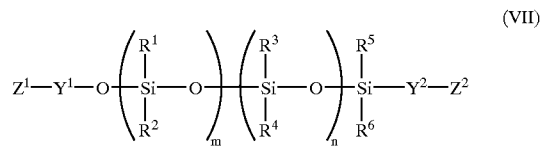

(VII)

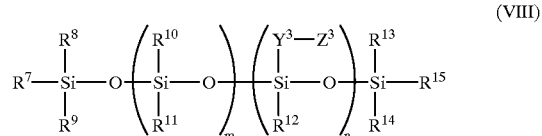

(VIII)

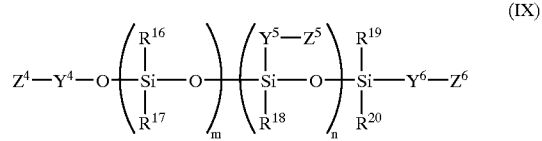

(IX)

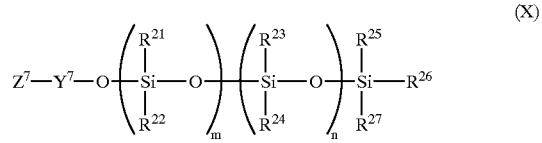

(X)

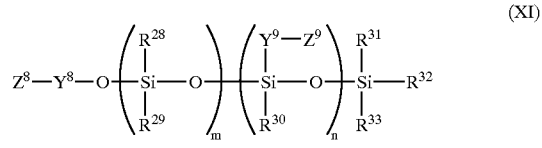

(XI)

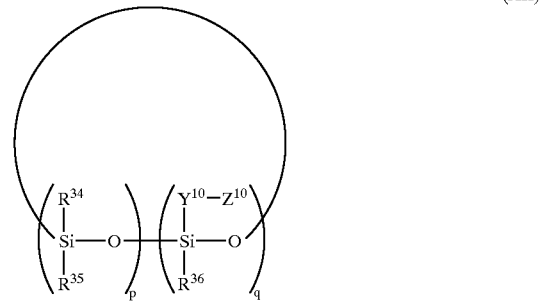

(XII)

(XIII)

where each $R^{1-38}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, polyether, or amino alkyl; $Z^{1-11}$, independently at each occurrence, is a molecular hook; and $Y^{1-11}$, independently at each occurrence, is a linker; wherein "m" in each formula has a value in a range between about 0 and about 13,000; "n" in each formula has a value in a range between about 0 and about 13,000 with the proviso that in formula (VIII) "n" is not 0; "m+n" in each formula has a value in a range between about 1 and about 26,000; "q" has a value of at least one; "p+q" has a value of at least 3; "a" has a value greater than or equal to one; and "b" and "g" have a value of at least one.

9. The composition in accordance with claim 8 comprising at least one compound of formulas (VII), (VIII), (IX), (X), or (XI), wherein $R^{1-33}$ is methyl; "m" in each formula has a value in a range between about 20 and about 120; "n" in each formula has a value in a range between about 2 and about 10; and "m+n" in each formula has a value in a range between about 15 and about 120.

10. The composition in accordance with claim 8 comprising at least one compound of formula (XII), wherein "q" has a value of at least one; "p+q" has a value in a range between about 3 and about 6; and $R^{34-36}$ is methyl.

11. The composition in accordance with claim 8, wherein the moiety Z—Y is prepared by a process which comprises combining a hook with a linker precursor comprising a linker and a leaving group.

12. The composition in accordance with claim 11, wherein the leaving group is selected from the group consisting of chloride, bromide, iodide, tosylate, mesylate, phosphate, and cyclic leaving groups containing at least one heteroatom.

13. The composition in accordance with claim 11, wherein the leaving group is iodide, chloride, or bromide.

14. The composition in accordance with claim 1, wherein the molecular hook comprises a heterocyclic pyridinium compound, a heterocyclic triazinium compound, a heterocyclic pyrimidinium compound, or a heterocyclic pyrazine compound.

15. The composition in accordance with claim 14, wherein the molecular hook is at least one member selected from the group consisting of a heterocyclic pyridinium compound (XIII), a heterocyclic triazinium compound (XIV), a heterocyclic pyrimidinium compound (XV), and a heterocyclic pyrazine compound (XVI):

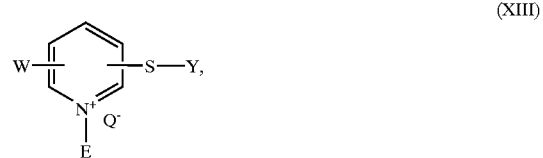

(XIII)

(XIV)

(XV)

-continued

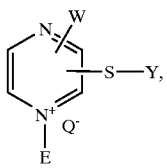
(XVI)

wherein Y is a linker; W is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N{=}NE^1$, $N{=}NOE^1$, $NE^1CN$, $N{=}C{=}NE^1$, $NE^1NE^2E^3$, $NE^1NA^2NA^3A^4$, $NA^1N{=}NE^2$; other groups including $CONE^1_2$, $CONE^1COE^2$, $C({=}NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be a silicone group, H, or any of the following: a straight, branched or mono- or polycyclic aliphatic, mono- or polyunsaturated alkyl, aryl, heteroalkyl, heteroaliphatic or heteroolefinic molecule including in a range between about 1 and about 30 carbon atoms together with heteroatoms in a range between about 0 and about 15, including oxygen, nitrogen, sulfur, phosphorus, silicon and incorporating one or more substituents including mono, poly or perfluoro substitution; and wherein the counterion, $Q^-$, is selected from the group consisting of halides, borates, phosphates, tosylates, mesylates, and triflates.

16. A hair care product comprising the composition of claim 1.

17. A textile care product comprising the composition of claim 1.

18. A cosmetic product comprising the composition of claim 1.

19. An oral care product comprising the composition of claim 1.

20. An animal care product comprising the composition of claim 1.

21. A method for providing adhesion of polysiloxane or silicone resin to hair which comprises treating hair with the composition of claim 1.

22. A silicone composition comprising at least one compound of the formula (VIII):

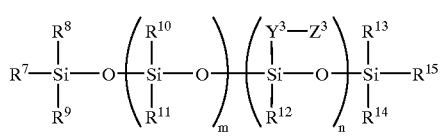
(VIII)

where each $R^{7-15}$ is methyl; $Z^3$ is a pyrimidinium molecular hook of the formula (XV)

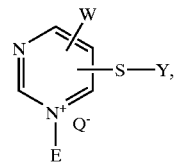
(XV)

wherein W is hydrogen, E is methyl; $Q^-$ is iodide, chloride, or bromide; and Y is at least one moiety of the formulas (I), (II), (III), (IV), (V), or (VI):

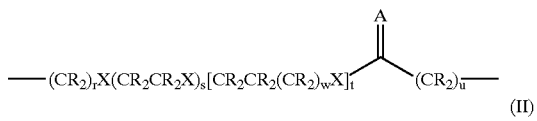
(I)

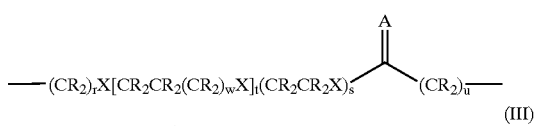
(II)

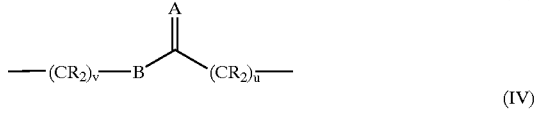
(III)

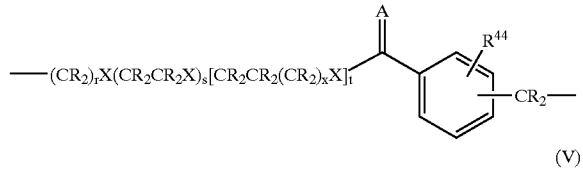
(IV)

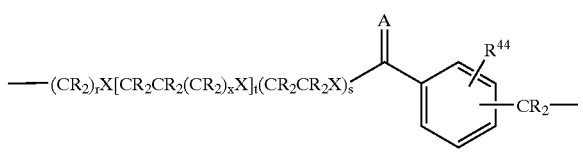
(V)

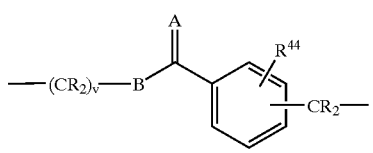
(VI)

wherein "m" is in a range between about 20 and about 120; "n" is in a range between about 2 and about 10; r is 2 or 3; s is in a range between about 4 and about 20; t is 0; u is 1; v is 2 or 3; w is 1 or 2; x is 1 or 2; X is O; R is H; $R^{44}$ is H; A is O; B is O;

and where the polysiloxane is bound to the $(CR_2)_r$ (Formula I, II, IV, and V) or $(CR_2)_v$ (Formula III and VI).

23. A hair care product comprising the composition of claim 22.

24. A method for providing adhesion of polysiloxane to hair which comprises treating hair with the composition of claim 22.

25. A silicone composition comprising at least one compound of the formula (VII):

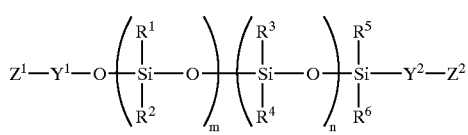

(VII)

where each $R^{1-6}$ is methyl; $Z^{1-2}$ are each a pyrimidinium molecular hook of the formula (XIV):

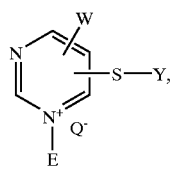

(XIV)

wherein W is hydrogen, E is methyl; $Q^-$ is iodide, chloride, or bromide; and Y is at least one moiety of the formulas (I), (II), (III), (IV), (V), or (VI):

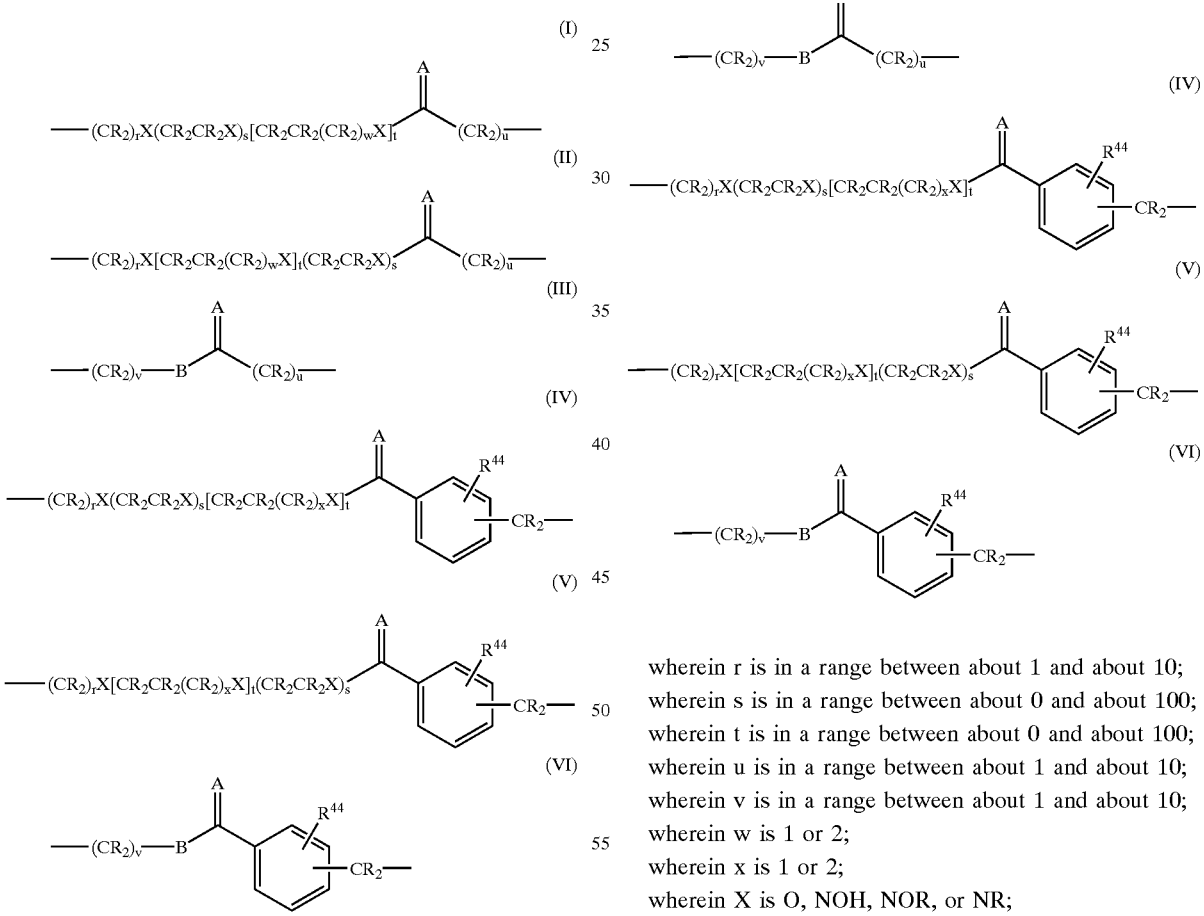

wherein "m+n" has a value in a range between about 20 and about 120; r is 2 or 3; s is in a range between about 4 and about 20; t is 0; u is 1; v is 2 or 3; w is 1 or 2; x is 1 or 2; X is O; R is H; $R^{44}$ is H; A is O; B is O; and where the polysiloxane is bound to the $(CR_2)_r$ (Formula I, II, IV, and V) or $(CR_2)_v$ (Formula III and VI).

26. A hair care product comprising the composition of claim 25.

27. A method for providing adhesion of polysiloxane to hair which comprises treating hair with the composition of claim 25.

28. A method for making a silicone composition comprising at least one polysiloxane or silicone resin, at least one linker, and at least one molecular hook, which method comprises combining a linker, a molecular hook, and a polysiloxane or silicone resin wherein the linker comprises at least one moiety of the formulas (I), (II), (III), (IV), (V), or (VI):

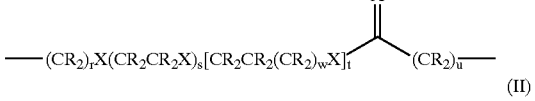

(I)

(II)

(III)

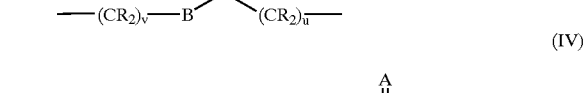

(IV)

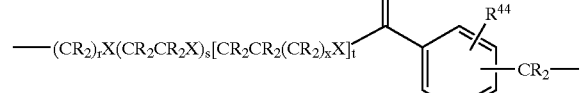

(V)

(VI)

wherein r is in a range between about 1 and about 10;
wherein s is in a range between about 0 and about 100;
wherein t is in a range between about 0 and about 100;
wherein u is in a range between about 1 and about 10;
wherein v is in a range between about 1 and about 10;
wherein w is 1 or 2;
wherein x is 1 or 2;
wherein X is O, NOH, NOR, or NR;
wherein R is independently at each occurrence hydrogen (H), $C_{1-22}$ alkyl, $C_{1-22}$ alkoxy, $C_{2-22}$ alkenyl, $C_{6-14}$ aryl, and $C_{6-22}$ alkyl-substituted aryl, and $C_{6-22}$ aralkyl where the C can be unsubstituted or substituted with heteroatoms such as oxygen (O), nitrogen (N), sulfur (S) or halogen;
wherein $R^{44}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, and ring system which may or may not be fused to the phenyl group where the C can be fused unsubstituted or substituted with heteroatoms such as O, N, S or halogen;

A=O, NOH, NOR, NR or S;

B=O, NOH, NOR, NR or S;

and where the polysiloxane or silicone resin is bound to the $(CR_2)_r$ (Formula I, II, IV, and V) or $(CR_2)_v$ (Formula III and VI).

29. The method in accordance with claim 28, wherein r is 2 or 3; s is in a range between about 4 and about 20; t is 0; u is 1; v is 2 or 3; w is 1 or 2; x is 1 or 2; X is O; R is H; $R^{44}$ is H; A is O; and B is O.

30. The method of claim 29 which comprises combining at least one linker with a polysiloxane or silicone resin and subsequently combining said combination with at least one molecular hook.

31. The method of claim 29 which comprises combining at least one linker with at least one molecular hook and subsequently combining said combination with a polysiloxane or silicone resin.

32. The method of claim 28 in which the at least one linker is bound to a polysiloxane or silicone resin through a silicon, carbon, oxygen, nitrogen, or sulfur atom.

33. The method of claim 32 in which the at least one linker is bound to a polysiloxane or silicone resin through a silicon atom.

34. The method of claim 28 in which the at least one polysiloxane or silicone resin comprises at least one compound of the following formulas, (VII), (VIII), (IX), (X), (XI), (XII), or (XIII):

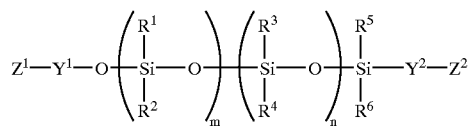
(VII)

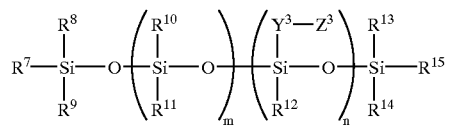
(VIII)

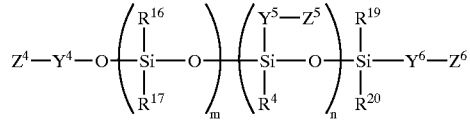
(IX)

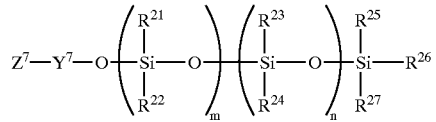
(X)

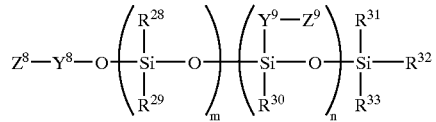
(XI)

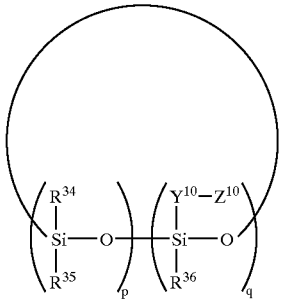
(XII)

$(R^{37}_3SiO_{1/2})_a[(Z—Y)R^{38}_2SiO_{1/2}]_b(SiO_{4/2})_g$ (XIII)

where each $R^{1-38}$ is independently at each occurrence a hydrogen atom, $C_{1-22}$ alkyl, $C_{1-22}$ alkoxy, $C_{2-22}$ alkenyl, $C_{6-14}$ aryl, and $C_{6-22}$ alkyl-substituted aryl, $C_{6-22}$ aralkyl, and $C_{1-22}$ fluoroalkyl, polyether, or amino alkyl; $Z^{1-10}$, independently at each occurrence, is the molecular hook; and $Y^{1-10}$, independently at each occurrence, is the linker; wherein "m" in each formula has a value in a range between about 0 and about 13,000; "n" in each formula has a value in a range between about 0 and about 13,000 with the proviso that in formula (VIII) "n" is not 0; "m+n" in each formula has a value in a range between about 1 and about 26,000; "q" has a value of at least one; "p+q" has a value of at least 3; "a" has a value greater than or equal to one; and "b" and "g" have a value of at least one.

35. The method of claim 34, wherein the polysiloxane comprises at least one compound of formulas (VII), (VIII), (IX), (X), or (XI), wherein $R^{1-33}$ is methyl; "m" in each formula has a value in a range between about 20 and about 120; "n" in each formula has a value in a range between about 2 and about 10; and "m+n" in each formula has a value in a range between about 15 and about 120.

36. The method of claim 34, wherein the polysiloxane comprises at least one compound of formula (XII), wherein "q" has a value of at least one; "p+q" has a value in a range between about 3 and about 6; and $R^{34-36}$ is methyl.

37. The method of claim 34 in which the average number of Y—Z moieties on a polysiloxane or silicone resin is in a range between about 1 and about 100.

38. The method of claim 37 in which the average number of Y—Z moieties on a polysiloxane or silicone resin is in a range between about 1 and about 10.

39. The method of claim 34, wherein the moiety Z—Y is prepared by a process which comprises combining a hook with a linker precursor comprising a linker and a leaving group.

40. The method of claim 39, wherein the leaving group is selected from the group consisting of chloride, bromide, iodide, tosylate, mesylate, phosphate, and cyclic leaving groups containing at least one heteroatom.

41. The method of claim 40, wherein the leaving group is iodide, chloride, or bromide.

42. The method of claim 28, wherein the molecular hook comprises a heterocyclic pyridinium compound, a heterocyclic triazinium compound, a heterocyclic pyrimidinium compound, or a heterocyclic pyrazine compound.

43. The method of claim 42, wherein the molecular hook is at least one member selected from the group consisting of a heterocyclic pyridinium compound (XIII), a heterocyclic triazinium compound (XIV), a heterocyclic pyrimidinium compound (XV), or a heterocyclic pyrazine compound (XVI):

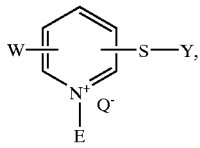
(XIII)

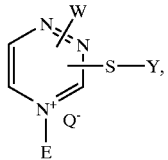
(XIV)

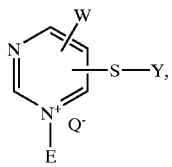
(XV)

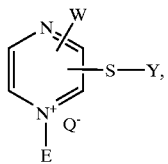
(XVI)

wherein Y is a linker; W is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^1$; O-linked groups including $OE^1$, OCN, $ONE^1E^2$; N-linked groups including $NE^1E$, $NE^1E^2E^{3+}$, $NE^1OE^2$, $NE^1SE^2$, NCO, NCS, $NO_2$, $N=NA^1$, $N=NOE^1$, $NE^1CN$, $N=C=NE^1$, $NE^1NE^2E^3$, $NE^1NE^2NE^3E^4$, $NE^1N=NE^2$; other groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be a silicone group, H or any of the following: a straight, branched or mono- or polycyclic aliphatic, mono- or polyunsaturated alkyl, aryl, heteroalkyl, heteroaliphatic or heteroolefinic system including in a range between about 1 and about 30 carbon atoms together with heteroatoms in a range between about 0 and about 15, including oxygen, nitrogen, sulfur, phosphorus, silicon and incorporating one or more substituents including mono, poly or perfluoro substitution; and wherein the counterion, $Q^−$, is selected from the group consisting of halides, borates, phosphates, tosylates, mesylates, and triflates.

44. A method for making a silicone composition comprising combining at least one linker with a polysiloxane and subsequently combining said combination with at least one molecular hook, wherein the polysiloxane is of the formula (VIII):

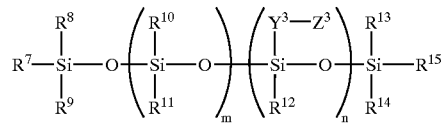
(VIII)

where each $R^{7-15}$ is methyl; $Z^3$ is a pyrimidinium molecular hook of the formula (XV)

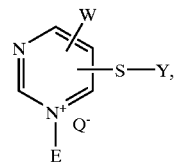
(XV)

wherein W is hydrogen, E is methyl; $Q^−$ is iodide; and Y is at least one moiety of the formulas (I), (II), (III), (IV), (V), or (VI):

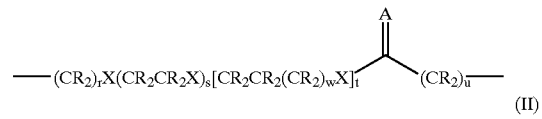
(I)

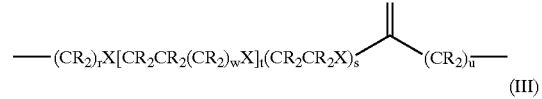
(II)

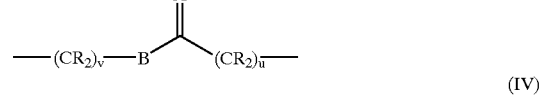
(III)

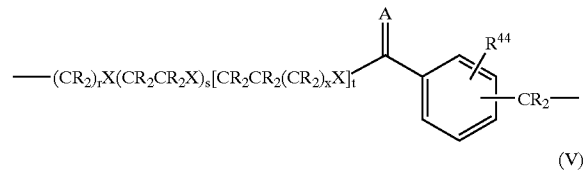
(IV)

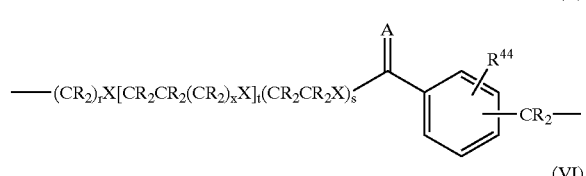
(V)

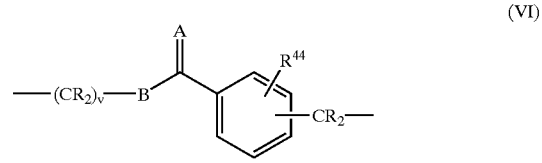
(VI)

wherein "m" is in a range between about 20 and about 120; "n" is in a range between about 2 and about 10; r is 2 or 3; s is in a range between about 4 and about 20; t is 0; u is 1; v is 2 or 3; w is 1 or 2; x is 1 or 2; X is O; R is H; $R^{44}$ is H; A is O; B is O; and where the polysiloxane is bound to the $(CR_2)_r$ (Formula I, II, IV, and V) or $(CR_2)_v$ (Formula III and VI).

45. A method for making a silicone composition comprising combining at least one linker with a polysiloxane and subsequently combining said combination with at least one molecular hook, wherein the polysiloxane is of the formula (VII):

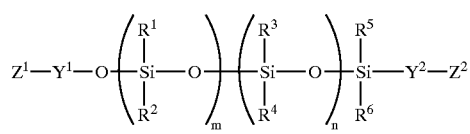
(VII)

where each $R^{1-6}$ is methyl; $Z^{1-2}$ are each a pyrimidinium molecular hook of the formula (XIV)

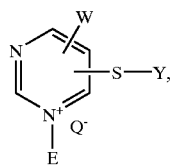
(XIV)

wherein W is hydrogen, E is methyl; $Q^-$ is iodide, chloride, or bromide; and Y is at least one moiety of the formulas (I), (II), (III), (IV), (V), or (VI):

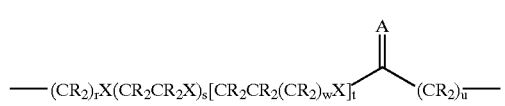
(I)

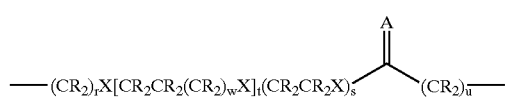
(II)

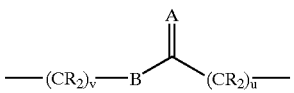
(III)

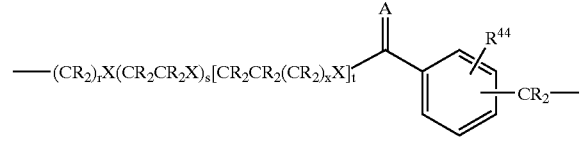
(IV)

(V)

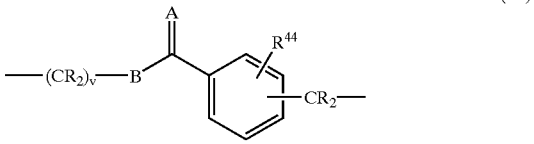
(VI)

wherein "m+n" has a value in a range between about 15 and about 120; r is 2 or 3; s is in a range between about 4 and about 20; t is 0; u is 1; v is 2 or 3; w is 1 or 2; x is 1 or 2; X is O; R is H; $R^{44}$ is H; A is O; B is O; and where the polysiloxane is bound to the $(CR_2)_r$ (Formula I, II, IV, and V) or $(CR_2)_v$ (Formula III and VI).

* * * * *